United States Patent
Le et al.

(10) Patent No.: US 9,622,660 B2
(45) Date of Patent: Apr. 18, 2017

(54) SYSTEM AND METHOD FOR ENABLING COLLABORATIVE ANALYSIS OF A BIOSIGNAL

(71) Applicant: Emotiv Lifesciences Inc., San Francisco, CA (US)

(72) Inventors: Tan Le, San Francisco, CA (US); Geoffrey Mackellar, San Francisco, CA (US)

(73) Assignee: Emotiv Lifesciences Inc., San Francisco, CA (US)

( * ) Notice: Subject to any disclaimer, the term of this patent is extended or adjusted under 35 U.S.C. 154(b) by 689 days.

(21) Appl. No.: 13/903,861

(22) Filed: May 28, 2013

(65) Prior Publication Data

US 2013/0314243 A1    Nov. 28, 2013

Related U.S. Application Data

(60) Provisional application No. 61/652,047, filed on May 25, 2012.

(51) Int. Cl.
  *A61B 5/04*  (2006.01)
  *A61B 5/00*  (2006.01)
  (Continued)

(52) U.S. Cl.
  CPC .......... *A61B 5/0002* (2013.01); *A61B 5/0006* (2013.01); *A61B 5/04012* (2013.01);
  (Continued)

(58) Field of Classification Search
  CPC . A61B 5/0002; A61B 5/0006; A61B 5/04012; A61B 5/0484; A61B 5/165; A61B 5/6803
  See application file for complete search history.

(56) References Cited

U.S. PATENT DOCUMENTS 4,421,122 A    12/1983 Duffy
6,230,049 B1    5/2001 Fischell et al.
(Continued)

FOREIGN PATENT DOCUMENTS

WO    2010147913 A1    12/2010

OTHER PUBLICATIONS

Park, et al. "Multiscale Entropy Analysis of EEG from Patients Under Different Pathological Conditions." Fractais 15, 399 (2007).
(Continued)

*Primary Examiner* — Etsub Berhanu
(74) *Attorney, Agent, or Firm* — Jeffrey Schox; Ivan Wong (57) ABSTRACT

A method and system for enabling collaborative analysis of biosignal data comprising: collecting a bioelectrical signal dataset from a first user; transmitting the bioelectrical signal dataset to a second user; generating an analysis based upon the bioelectrical signal data; transmitting the analysis to at least one of the first user and a third entity; and facilitating a communication, related to the analysis, between at least two of the second user, the first user, and the third entity. The method can further comprise providing a stimulus configured to prompt the action; and providing a modified stimulus to the first user based upon at least one of the analysis and the communication. An embodiment of the system comprises a biosignal detector and a processor configured to implement an embodiment of the method.

19 Claims, 6 Drawing Sheets (51) Int. Cl.
*A61B 5/0484* (2006.01)
*A61B 5/16* (2006.01)

(52) U.S. Cl.
CPC ............ *A61B 5/0484* (2013.01); *A61B 5/165* (2013.01); *A61B 5/6803* (2013.01)

(56) References Cited

U.S. PATENT DOCUMENTS

| | | | |
|---|---|---|---|
| 6,954,700 B2 | 10/2005 | Higashida et al. | |
| 7,844,324 B2 | 11/2010 | Saerkelae et al. | |
| 7,904,144 B2 * | 3/2011 | Causevic | A61B 5/048 600/544 |
| 7,962,204 B2 | 6/2011 | Suffin et al. | |
| 7,986,991 B2 | 7/2011 | Prichep | |
| 8,103,333 B2 | 1/2012 | Tran | |
| 8,108,036 B2 | 1/2012 | Tran | |
| 8,114,021 B2 | 2/2012 | Robertson et al. | |
| 8,147,419 B2 | 4/2012 | Krauss et al. | |
| 8,190,248 B2 | 5/2012 | Besio et al. | |
| 8,190,249 B1 | 5/2012 | Gharieb et al. | |
| 2003/0055355 A1 | 3/2003 | Viertio-Oja | |
| 2004/0078219 A1 * | 4/2004 | Kaylor | G06Q 50/22 705/2 |
| 2004/0249249 A1 * | 12/2004 | Lawson | A61B 5/02405 600/300 |
| 2005/0240087 A1 * | 10/2005 | Keenan | A61B 5/0456 600/301 |
| 2005/0283053 A1 * | 12/2005 | deCharms | A61B 5/055 600/300 |
| 2006/0009697 A1 * | 1/2006 | Banet | A61B 5/0002 600/485 |
| 2006/0063980 A1 | 3/2006 | Hwang et al. | |
| 2006/0173510 A1 | 8/2006 | Besio et al. | |
| 2007/0061735 A1 * | 3/2007 | Hoffberg | G06F 9/4443 715/744 |
| 2007/0100246 A1 | 5/2007 | Hyde | |
| 2007/0150025 A1 * | 6/2007 | Dilorenzo | A61B 5/0476 607/45 |
| 2007/0208263 A1 | 9/2007 | John et al. | |
| 2007/0219455 A1 | 9/2007 | Wong et al. | |
| 2008/0108908 A1 * | 5/2008 | Maddess | A61B 5/04842 600/544 |
| 2008/0146890 A1 | 6/2008 | Leboeuf et al. | |
| 2008/0177197 A1 * | 7/2008 | Lee | A61B 5/165 600/545 |
| 2009/0018405 A1 | 1/2009 | Katsumura et al. | |
| 2009/0024050 A1 | 1/2009 | Jung et al. | |
| 2009/0062676 A1 | 3/2009 | Kruglikov et al. | |
| 2009/0214060 A1 * | 8/2009 | Chuang | A61B 5/0478 381/151 |
| 2009/0247894 A1 * | 10/2009 | Causevic | A61B 5/0478 600/544 |
| 2009/0292180 A1 | 11/2009 | Mirow | |
| 2009/0318825 A1 | 12/2009 | Kilborn | |
| 2010/0010336 A1 | 1/2010 | Pettegrew et al. | |
| 2010/0010364 A1 | 1/2010 | Verbitskiy | |
| 2010/0022820 A1 | 1/2010 | Leuthardt et al. | |
| 2010/0022907 A1 | 1/2010 | Perez-Velazquez et al. | |
| 2010/0042011 A1 | 2/2010 | Doidge et al. | |
| 2010/0049004 A1 | 2/2010 | Edman et al. | |
| 2010/0169409 A1 | 7/2010 | Fallon et al. | |
| 2010/0286549 A1 | 11/2010 | John et al. | |
| 2011/0071364 A1 | 3/2011 | Kuo et al. | |
| 2011/0087125 A1 * | 4/2011 | Causevic | A61B 5/04 600/544 |
| 2011/0184247 A1 | 7/2011 | Contant et al. | |
| 2011/0245633 A1 | 10/2011 | Goldberg et al. | |
| 2011/0270117 A1 | 11/2011 | Warwick et al. | |

OTHER PUBLICATIONS

Stam et al., Nonlinear Synchronization in EEG and Whole-Head MEG Recordings of Healthy Subjects, date unknown.

\* cited by examiner

SYSTEM AND METHOD FOR ENABLING COLLABORATIVE ANALYSIS OF A BIOSIGNAL

CROSS-REFERENCE TO RELATED APPLICATIONS

This application claims the benefit of U.S. Provisional Application Ser. No. 61/652,047 filed 25 May 2012, which is incorporated in its entirety herein by this reference.

TECHNICAL FIELD

This invention relates generally to the biosignals field, and more specifically to a new and useful system and method for enabling collaborative analysis of biosignals in the biosignals field.

BACKGROUND

The general populace interacts with a wide variety of sensors on a daily basis, and vast amounts of data pertaining to individuals and entire groups of people is collected from these sensors. This data can be anchored in the physical realm, such as location data provided through a GPS sensor, caloric expenditure provided by an exercise machine, footstep count provided by an accelerometer-based step counter, or heart rate, body temperature, respiratory rate, or glucose level provided by a biometric sensor. This data can also be anchored in the digital realm, such as interests as indicated by websites visited or needs as indicated by purchases made through an online store. This data can provide significant insight into market trends, needs, interests, health, and development of an individual or particular demographic. However, contemporary sensors, data collection, and data analysis fail to capture cognitive, mental, and affective states of individuals and groups of people that can provide similar insight. Furthermore, contemporary data collection fails to efficiently locate, obtain, and aggregate biosignal data from multiple or selected individuals and make this data available for analysis. Therefore there is a need in the biosignals field for a new and useful system and method for enabling collaborative analysis of a biosignal.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1A:
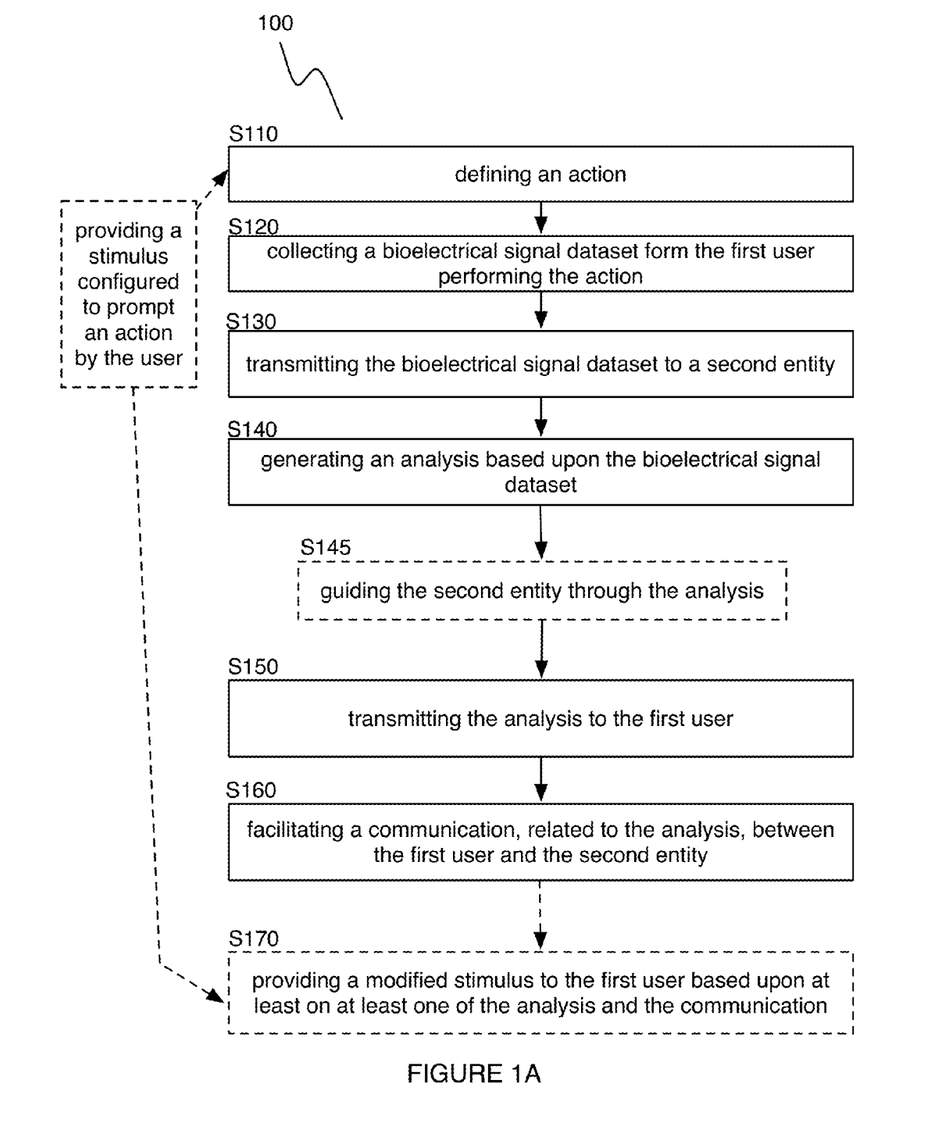
FIG. 1A is a flowchart representation of an embodiment of a method for instructing a behavior change in a user.
Figure 1B:
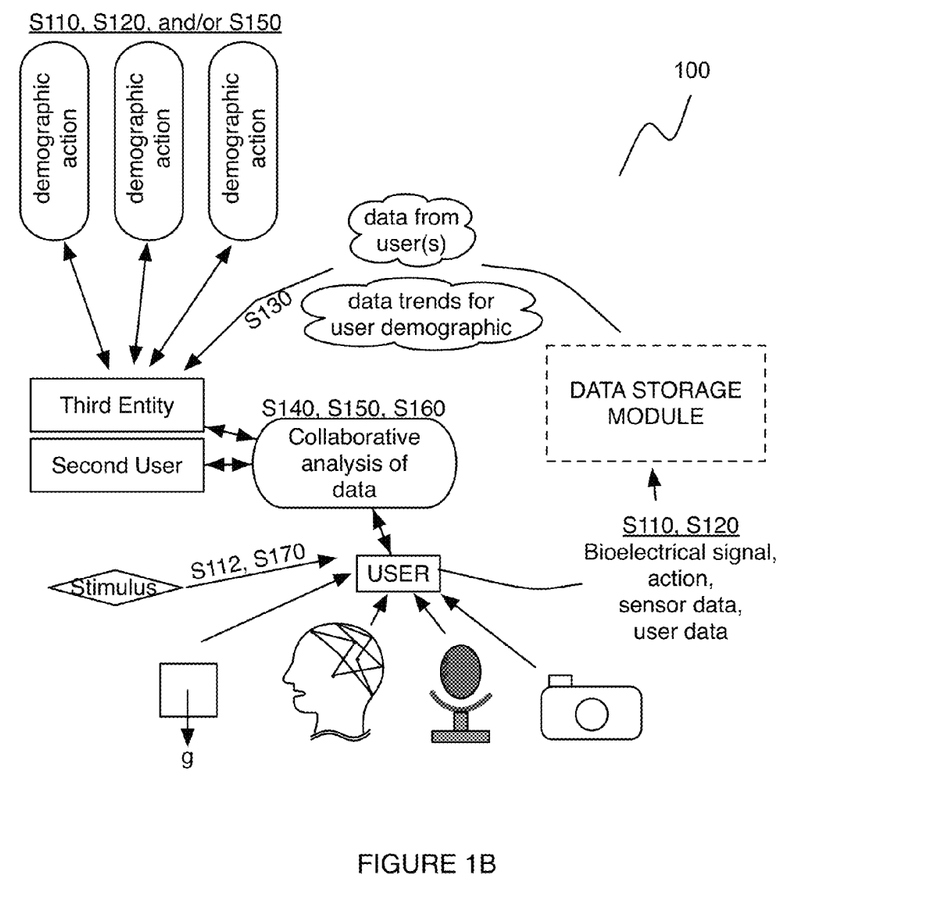
FIG. 1B is a schematic of an embodiment of a method for instructing a behavior change in a user.

As shown in FIGS. 1A and 1B, an embodiment of a method 100 for enabling collaborative analysis of biosignal data of a first user comprises defining an action S110; collecting a bioelectrical signal dataset from the first user as the first user performs the action S120, transmitting the bioelectrical signal dataset to a second user S130, generating an analysis based upon the bioelectrical signal dataset S140, transmitting the analysis to at least one of the first user and a third entity S150, and facilitating a communication, related to the analysis, between at least two of the second user, the first user, and the third entity S160.

The method 100 functions to enable collaborative analysis of biosignal data based upon bioelectrical signal data and other data (e.g., biometric data, user environment data) collected from a user while the user performs a particular action or responds to a stimulus. The method 100 therefore preferably enables users to connect over collected biosignal data; to collaboratively research causes, symptoms, and changes in brain function; to facilitate a behavior change in any suitable environment of the user or in any suitable manner; and/or to communicate and share insights into mental development and behaviors affecting brain function. The method 100 can thus embody a form of telemedicine, such as with an emphasis on brain function, mental disorders, and/or mental health. Any of the research pertinent to or analysis of the bioelectrical signal data can be specific to a particular user (e.g., the first user) or general to a population or demographic. For example, collected data can be used to diagnose a mental disorder in the first user or to tailor a curriculum for a certain group of students of a certain demographic or character trait. However, the collected data and method 100 can be used in any other way. Preferably, the method 100 involves collection and analysis of data from the user outside of a clinical (e.g., hospital, therapy center) or research (e.g., laboratory) environment using portable devices. Additionally, the analyses, and/or communications are preferably performed in relation to data collected at multiple time points and/or under different circumstances (e.g., actions or activities). Thus, periodic reports of one or more users can define indicators (e.g., indicators related to brain function) that can be projected forward to teach longitudinal trends or insights for the one or more users.

As shown in FIG. 1B, a third entity can perform portions of an embodiment of the method 100. Prior to transmitting the bioelectrical signal dataset in Step S130, the third entity preferably accesses the bioelectrical signal data of the first user through an application programming interface (API) hosted by or in communication with a data storage module (e.g., remote server, cloud, local storage). The third entity can also access past bioelectrical signal data or other data of the first user and/or aggregate data of other users through the API. The third entity can be a remote server, local network, website, mobile application, or other suitable entity that hosts audio-, video-, and/or text-based communication between the first and second users. Generally, the third entity is preferably implemented as an application ('app') and/or a web portal accessible on multiple electronic devices, including an electronic device of the first user and on an electronic device of the second user. Each electronic device is preferably a mobile electronic device, such as a smartphone, a tablet, a laptop computer, a personal data assistance (PDA), a digital music player, or a digital watch, though the electronic device can be any other suitable electronic device, such as a desktop computer, a gaming console, or an in-dash display in a vehicle. However, EEG data can be collected and accessed in any other way by any other entity or electronic device.

Figure 6:
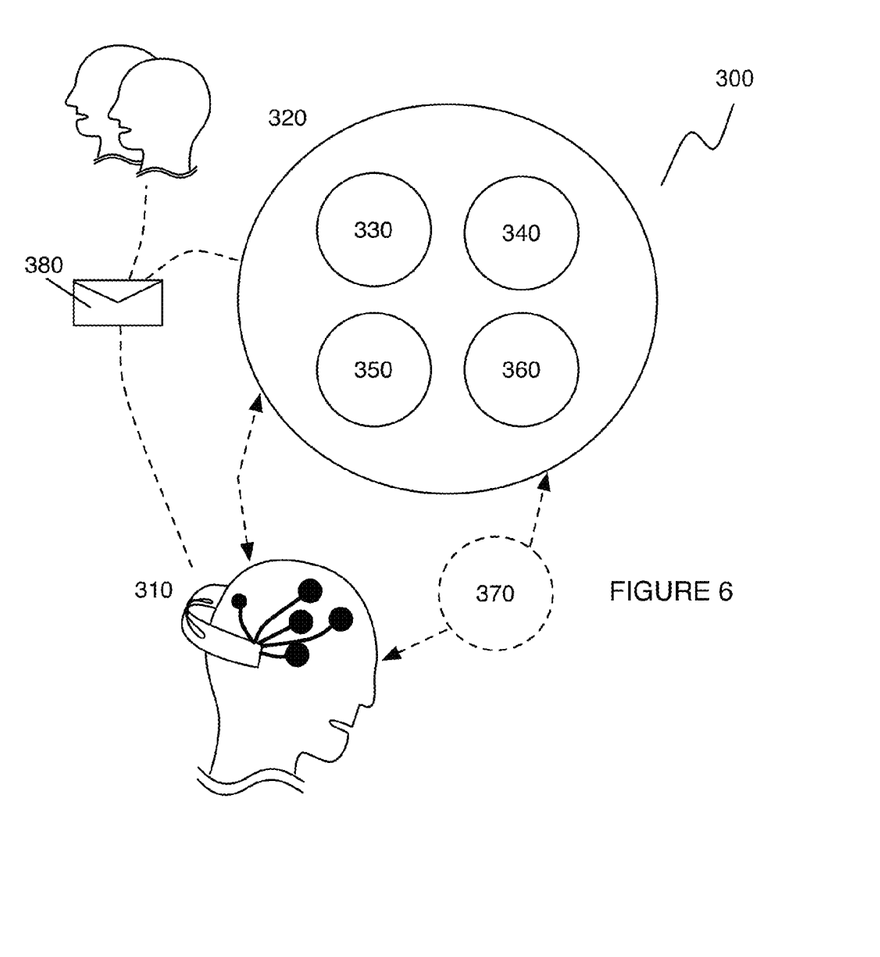
FIG. 6 is a schematic of an embodiment of a system for instructing a behavior change in a user.

In variations of the method 100, the method 100 can be used to enable analyses and communications between a health care professional and a patient or between multiple users of a given demographic group (e.g., group characterized by age, gender, ethnicity, health condition, geographic location, etc.) in order to provide analyses relevant to the wellbeing of the user. The method 100 is preferably performed using an embodiment of a system 300 comprising a biosignal detector 310 and a processor 320 coupled to a user interface 325, wherein the processor comprises a receiver 330, an analyzer 340, a transmitter 350, and a stimulus transmission module 360, as described in further detail below; however, the method 100 can be performed using any suitable system configured to collect bioelectrical signal data from a user and generate an analysis based upon the bioelectrical signal data.

Step S110 recites defining an action, and functions to enable coupling of an action performed by a user with a bioelectrical signal dataset collected from the user while the user performs the action. The action of Step S110 can further function to define a window (e.g., a window of time) for bioelectrical signal collection, wherein the window encompasses bioelectrical signals captured while a user or group of users engages in the action. Step S110 preferably includes defining at least one of an active and/or a passive action, but can additionally or alternatively include any other suitable action performed by a user. Examples of active actions include playing an instrument, driving a car, conversing, writing, reading, studying, eating, cooking, surfing the web, and exercising. Examples of passive actions include sleeping, resting, listening to music, and watching television. Other suitable actions performed by the user may comprise involuntary actions, such as evoked signals and reflex reactions, and may be characterized by reaction times or other parameters relevant to reaction responses.

Step S110 can further comprise providing a stimulus S112, as shown in FIG. 1A, which functions to generate or prompt a bioelectrical signal response (i.e., an action) in a user or group of users that can be collected and analyzed. The stimulus can be provided in any suitable manner, can be automatically or manually provided, and can be provided to multiple users (e.g., a demographic group) simultaneously or non-simultaneously. Furthermore, multiple stimuli can be provided, such that responses to combined stimuli and/or a sequence of stimuli can be later analyzed. The stimulus can be a notification, a command to perform an action, a haptic stimulus, a visual stimulus, an auditory stimulus, an environmental stimulus, or any other suitable stimulus. Furthermore, the stimulus can be time-locked (i.e., provided and/or presented within a specific time window characterized by an initiation time and a termination time) and/or presented at multiple timepoints to individual users. Additionally, provision of the stimulus/stimuli can be synchronized with user biosignal, biometric, and/or environment data substantially in real time, or upon detection of an event from user biosignal, biometric, and/or environment data. In one variation, the stimulus is provided using a mobile device of the user, or a set of mobile devices of a group of users, such that the stimulus can be provided at any point that a user or group of users is using the mobile device(s).

In a first example, the stimulus is a command provided on a mobile device application that tells a user to go to a specific nearby restaurant (based upon received GPS data) and eat a specific menu item. In a second example, the stimulus is a music piece that is automatically provided on a mobile device action, such that a reaction response to the music piece, captured in bioelectrical signal data collected from a user, can be analyzed. In a third example, the stimulus is a disturbing news story provided on a mobile device, such that a reaction response to the news story can be analyzed. In a fourth example, a combination of stimuli can be provided, such as a happy image rendered on a mobile device display followed by a sad music piece, such that reactions to combinations of stimuli can be later analyzed. In a fifth example, the stimulus can be a medication dosage provided automatically or manually, such that bioelectrical signal data associated with the user's response to the medication can be collected and analyzed. In a sixth example, the stimulus or combination of stimuli comprise therapeutic stimuli for relieving a psychological disorder of the user, such that the response to the stimulus/stimuli can be captured in the bioelectrical signal data collected from the user. In a seventh example, the stimulus is automatically provided upon detection that a user is exercising, as determined from additional biosignal, biometric, and or environment data. Thus, Step S112 allows a stimulus or a combination of scriptable stimuli to be provided to a user or a group of users, which enables fully deployable automated experiments to be performed. In other variations and examples of Steps S110 and S112, defining the action and/or providing the stimulus can be performed according to methods described in U.S. patent application Ser. No. 13/903,806, entitled "System and Method for Providing and Aggregating Biosignals and Action Data" and U.S. patent application Ser. No. 13/903,832, entitled "System and Method for Instructing a Behavior Change in a User", which are incorporated herein in their entirety by this reference.

Step S120 recites collecting a bioelectrical signal dataset from the first user as the first user performs the action, and functions to receive data while a user performs an action relevant to the user's wellbeing, relevant to the user's demographic, and/or relevant to the user's interests. Preferably, the bioelectrical signal data includes electroencephalograph (EEG) data, which can be reflective of cognitive, mental, and affective state of the user. However, the bioelectrical signal data can additionally or alternatively include any one of more of: data related to magnetoencephalography (MEG) impedance or galvanic skin response (GSR), electrocardiography (ECG), heart rate variability (HRV), electrooculography (EOG), and electromyelography (EMG). Furthermore, Step S110 can comprise collecting other biosignal data, including data related to cerebral blood flow (CBF), optical signals (e.g., eye movement, body movement), mechanical signals (e.g., mechanomyographs) chemical signals (e.g., blood oxygenation), acoustic signals, temperature, respiratory rate, and/or any other data obtained from or related to biological tissue or biological processes of the user, as well as the environment of the user. Additionally, the bioelectrical signal data preferably includes data acquired from multiple channels, wherein each channel is associated with a particular sensor arranged on a particular location or region of the user (e.g., head region, torso region).

In one example of bioelectrical signal data collected in Step S120, one of more sensors for data collection can be primarily associated with a particular region of the brain. Brain activity can thus be collected from isolated regions of the brain, such as the forebrain, midbrain, and hindbrain, for particular regions of the brain, such as the frontal, temporal, parietal, or occipital lobes of the cerebral cortex, for more specific portions of the brain, such as the left or right parietal lobe, or for any other portion of the brain of any other focus. In other examples, the bioelectrical signal data can alternatively comprise a single signal (e.g., from a single channel or as a composite of multiple channels), or a plurality of composite signals, each of which is a composite of multiple channels. The bioelectrical signal can also be a compressed, filtered, analyzed, or otherwise processed version of raw bioelectrical signals from one or more sensors. However, the bioelectrical signal data can be of any other suitable form or format.

Figure 2:
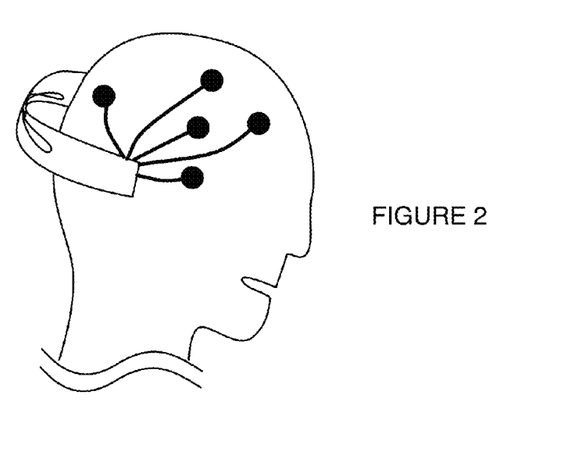
FIG. 2 depicts an embodiment of a biosignal detector.

In Step S120, collecting a bioelectrical signal dataset preferably comprises collecting a bioelectrical signal dataset at a biosignal detector that is worn by the user while he/she performs the action defined in Step S110. In one variation, Step S110 is performed using a portable biosignal detector that can operate outside of a clinical (e.g., hospital) or research (e.g., laboratory) setting, such that that the first user can be in a non-contrived environment as the bioelectrical signal dataset is collected and received. In another variation, Step S110 can be performed using a biosignal detector operating within a clinical or research setting. In a specific example of Step S110, the user wears a portable EEG device, an example of which is shown in FIG. 2, while performing a substantially normal, everyday activity, such as driving, playing a sport, shopping, working, studying, drawing reading, watching television, playing an instrument, or otherwise engaging in a substantially normal (e.g., daily) activity or action. In the specific example, the bioelectrical signal data (i.e., EEG signal data) is therefore collected while the user is outside of a hospital, lab, or purely medical setting and substantially removed from medical/research staff. Furthermore, in the specific example, stimuli and/or actions can then be coupled with EEG signal data associated with different portions of the brain.

Furthermore, in Step S120, the bioelectrical signal dataset can be collected as described above and stored locally prior to generation of an analysis in Step S140 or can be stored on a separate module in communication with the biosignal detector. In variations, the separate device can be a mobile electronic device, such as a smartphone, a tablet, a personal data assistant (PDA), a laptop, or a digital music player. In other variations, the separate device can be a non-mobile device, such as a desktop computer, a gaming console, or any other suitable device. The separate device in these variations is preferably Internet-capable (e.g., via a Wi-Fi, cellular, or Ethernet connection) such that the bioelectrical signal dataset can be subsequently transmitted to a data storage module, and can be accessed by a user or other entity; however, the bioelectrical signal dataset can be accessible in any other suitable manner. By accessing the bioelectrical signal dataset following recordation, the user or other entity can associate an action, activity, person, location, mood, weather, or other relevant personal or action-related information with the bioelectrical signal data. In a specific example, this information is automatically captured through a smartphone device that stores bioelectrical signal data (e.g., EEG data) locally, through a mobile application executing on the smartphone and in communication with the data storage module (i.e., module hosted at a remote server, cloud storage module. In another specific example, the user provides any of the foregoing personal or action-related information (or subsets of information) through a web browser or application executing on a non-mobile electronic device and in communication with the data storage module or through another venue, media, or method.

In Step S120, the bioelectrical signal dataset is preferably collected from a user while the user engages in or performs an action associated with the user's wellbeing or any other suitable action. Furthermore, collecting a bioelectrical signal dataset in Step S120 can be triggered manually (e.g., by manually activating a collection device) or automatically (e.g., in collaboration with supplementary biosignal sensor systems or upon wearing a biosignal detector) in other variations. In variations involving automatic triggering, initiation of bioelectrical signal data collection can be automatically coordinated with provision of a stimulus in Step S112, and/or termination of signal data collection can be automatically coordinated with termination of the stimulus.

In a further variation bioelectrical signal collection can be initiated semi-automatically when the user interacts with an interface device, such as a smartphone, tablet, or other electronic device. In this variation, the interaction with the interface device can also provide additional data relevant to the user and/or the analysis. In one example, an input provided by the user into an e-reader to move to a subsequent page indicates that the user is reading; and the title, genre, and/or other details of the book can also be accessed. In another example, a GPS sensor arranged within a vehicle determines that the user is driving and provides information related to the departure and present locations, from which a final destination and local traffic conditions can also be assembled, such as by accessing published traffic data and an electronic calendar of the user. However, any other device implementing any other sensor can be accessed to inform the action of the user and to initiate and/or terminate bioelectrical signal capture.

Again, any one or more of the aforementioned sensors, or any other sensor coupled to, in communication with, or integrated into a biosignal detector collecting bioelectrical signal data, can facilitate collection of bioelectrical signal data while the user performs an action in Step S120. Additional information associated with the action (e.g., an action tag, supplementary information) and sourced from external entities, by any user, or by an interface device, can also be associated with the bioelectrical signal data. For example, a digital medical record of the user, a profile of the user on a social network, a digital calendar of the user, or a sensor coupled to, in communication with, a GPS sensor on a mobile electronic device carried by the user, or integrated into a biosignal detector or other electronic device proximal to the first user can provide additional information to be associated with the action. This additional information can include age, gender, race, cultural background, interests, marital status, blood type, medical history, mental or physical illness, location, habits, other common actions and expected timings thereof, mood, diet, weather, book title, movie genre, or any other relevant personal, environment, or action-related information associated with the EEG signal. Therefore, information of various types and provided by various sources can enrich and augment bioelectrical signal data that is collected in Step S120 to produce an augmented dataset associated with the user. Additionally or alternatively, the bioelectrical signal data and enriching data can be added to compiled bioelectrical signal data of multiple users, and in this variation, the bioelectrical signal data and enriching data are preferably anonymized to conform to relevant privacy and security laws, such as the Health Insurance Portability and Accountability Act (HIPAA).

Figure 3:
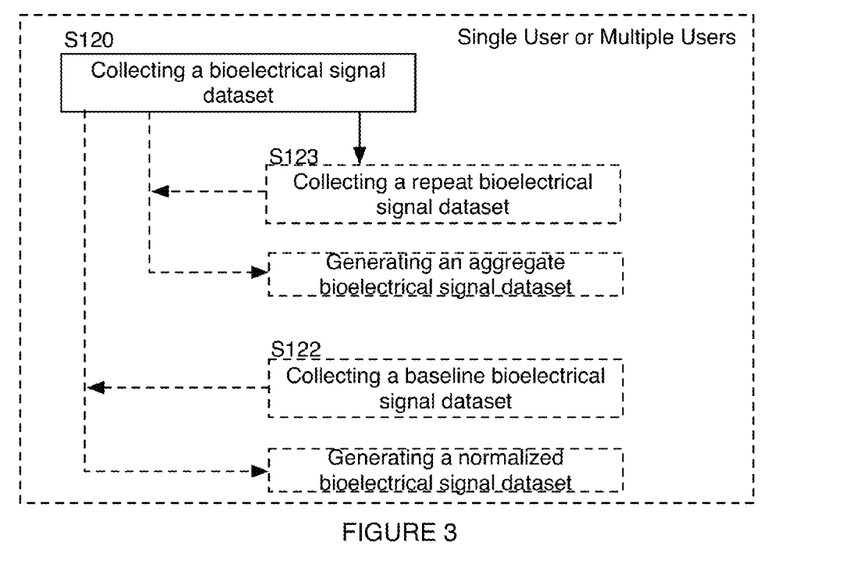
FIG. 3 is a flowchart representation of an embodiment of a portion of a method for instructing a behavior change in a user.

As described above in the variations and examples of Step S120, collecting the bioelectrical signal dataset preferably includes receiving bioelectrical signal data taken while the user performs an action relevant to the user's wellbeing/interests; however, as shown in FIG. 3, Step S120 can further include collecting a baseline bioelectrical signal dataset S122 and/or collecting a repeat bioelectrical signal dataset S123. Collecting a baseline bioelectrical signal dataset S122 can comprise collecting bioelectrical signal data while the user is in a neutral state, and functions to generate a baseline dataset against which other bioelectrical signal data from a user can be normalized or compared (e.g., to produce a normalized bioelectrical signal dataset). In a specific example of collecting a baseline bioelectrical signal dataset, a set of EEG data can be taken while the user is stationary with eyes closed for a period of time (e.g., thirty seconds) prior to collecting bioelectrical signal data while an action is being performed (e.g., between an action initiation time point and an action termination time point). However, the baseline bioelectrical signal dataset can be of any other suitable active or passive action of the user and the EEG signal can include any other relevant EEG data. Collecting a repeat bioelectrical signal dataset S123 functions to allow multiple bioelectrical signal datasets from a user to be collected and analyzed (e.g., to produce an aggregate bioelectrical signal dataset for a single user or multiple users). The repeat bioelectrical signal dataset(s) can be collected while a user repeats a specific action, such that multiple datasets characterizing a substantially identical action can be analyzed in a manner relevant to the user; however, the repeat bioelectrical signal dataset can be collected while the user performs a different action than a previously performed action. In one example, the bioelectrical signal dataset can be collected while the user is listening to music, and the repeat bioelectrical signal dataset can be collected while the user is playing an instrument, such that data for complementary actions can analyzed. In another example, the bioelectrical signal dataset can be collected while the user is mentally focused on a working task and the repeat bioelectrical signal dataset can be collected while the user is distracted, such that data for "opposite" actions can be analyzed to facilitate a behavior change. In this example, bioelectrical signal datasets associated with an action, paired with repeat bioelectrical signal datasets associated with a different action, acquired at substantially different time points (e.g., in Steps S110 and S110) can be analyzed for divergences in signal trends for the two actions, across the time points.

Figure 4:
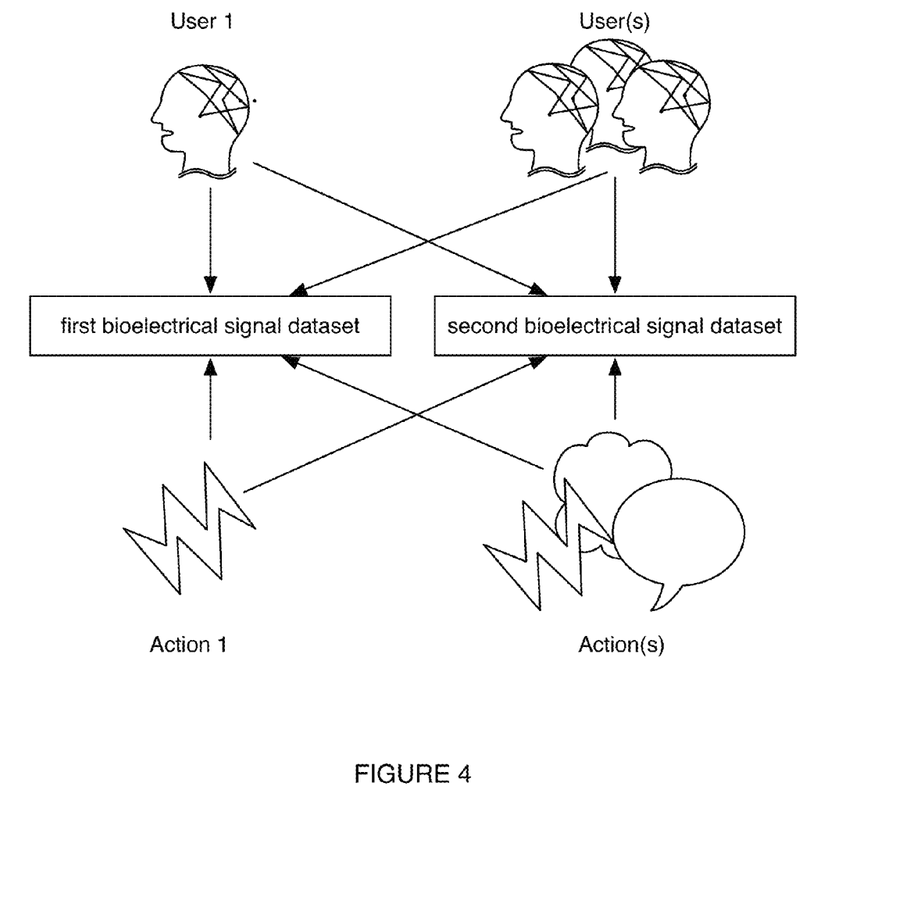
FIG. 4 is a flowchart representation of an embodiment of a portion of a method for instructing a behavior change in a user.

Variations of Steps S110 and S120 thus encompass conditions wherein the bioelectrical signal data are collected from a single user or multiple users, are associated with the same or different action(s), and/or are collected at multiple time points or within multiple time windows, as shown in FIG. 4. Additionally, Steps S110 and S120 can be performed according to any of the embodiments, variations, examples, or any combination thereof as described in U.S. patent application Ser. No. 13/903,806, entitled "System and Method for Providing and Aggregating Biosignals and Action Data", and U.S. patent application Ser. No. 13/903, 832, entitled "System and Method for Instructing a Behavior Change in a User".

Step S130 recites transmitting the bioelectrical signal dataset to a second user, and functions to initiate collaboration in analyzing the bioelectrical signal dataset associated with the first user. Preferably, the bioelectrical signal data and any suitable accompanying data (e.g., action information, an augmented dataset) is transmitted to and maintained by a data storage module and subsequently accessed by a third entity (remote server, local network, website, mobile application) for transmission to the second user in Step S130. Thus, the first and second users can interact through the third entity on a substantially one-on-one basis. Furthermore, the bioelectrical signal data and/or augmented data can be transmitted to the data storage module and/or to the second user substantially in real time, or the data can be transmitted to the second user substantially following completion of an action by the first user. Preferably, all or a portion of the data is transmitted in accordance with established privacy laws (e.g., HIPAA). In one variation of Step S130, data transmission to the second user is substantially automatic, wherein the data is transmitted to the second user during or after recordation without necessitating manual input (e.g., input from either of the first or second users). In another variation of Step S130, all or a portion of the data is transmitted to the second user only following release by the first user or other responsible entity, such as a parent, legal guardian, or health care provider of the first user. In yet another variation of Step S130, the data is transmitted to the second user upon a request by the second user or following an agreement between the first and second users. However, release and transmission of the data to the second user can follow any other schema or timing, and can be transmitted in any other suitable manner.

In Step S130, the data or a portion thereof is preferably transmitted to an electronic device of the second user. The electronic device of the second user is preferably Internet-capable and presents the relevant information in the EEG data to the second user via a web browser or application executing on the electronic device. The electronic device, web browser, and/or application preferably also supports video conferencing, audio conferencing, email, instant messaging, or other audio-, visual-, or text-based communication between the first and second users. This communication can be private, semi-private, or public, as preferably defined by at least one of the first and second users. Furthermore, transmission of data or any communication between the first and second users can be encrypted according to any of a variety of authentication and encryption schema. For example, cryptographic protocols such as Diffie-Hellman key exchange or Wireless Transport Layer Security (WTLS), or encryption standards, such as Data Encryption Standard (DES), Triple Data Encryption Standard (3-DES), or Advanced Encryption Standard (AES), can be implemented. However, EEG data and any other suitable information can be transmitted to the second user in any other suitable manner.

The first and second users can also be related in any suitable way, as described in several examples as follows: In one example, the first user is a patient of the second user who is a doctor, and the doctor can receive data for the first user that can be analyzed to aid the doctor in diagnosing a mental condition of the first user. In this example, the preferred method can embody a form of telemedicine, such as with an emphasis on brain function, mental disorders, and/or mental health. In another example, the first and second users are strangers but are grouped together (either automatically or manually) based upon a shared demographic, mental or physical illness or disorder, interest, etc., or based upon similarities or differences in biosignal data for a given activity. In this example, Step S130 can also include transmitting data of the second user to the first user and transmitting an analysis of the data of the second user, by the first user (or other entity), to the second user. Thus, in this example, the first and second users can collaborate to characterize brain function and/or trends in brain activity based upon commonalities (or differences) or shared characteristics in the users. This can provide greater insight, such as for the scientific and medical communities at large, into correlations between brain function and certain character traits. In yet another example, the first user is an entity (e.g., child) dependent upon the second user and the method 100 is used to track mental development of the dependent and to gain quantitative and/or qualitative insight into parent-dependent interactions (e.g., interactions related to discipline, teaching, and habit enforcement). In a further example, the first user is a participant in a study managed by the second user or another entity for which the second user is a representative. However, the first and second users can be related in any other suitable manner. Furthermore, the second user is preferably a human but can alternatively be an automaton or automated script configured to generate an analysis of data from a user.

In Step S130, bioelectrical signal data and/or augmented data transmitted to the second user can additionally comprise bioelectrical signal data of multiple users that are captured over time and while the other users engage in an action or actions relevant to the action associated with the bioelectrical signal data of the first user. Through comparison of the bioelectrical signal data of the first user with bioelectrical signal data of other users, trends characterized within data of the first user can thus be compared to or against data from other users. In a few examples, the aggregation of data can facilitate variations of Step S140 to generate analyses (e.g., quantitative, qualitative, and/or comparative analyses) that characterize mental development of the first user, characterize the presence and/or level of mental disorder in the first user, characterize expectations of mental advancement of the first user, provide insight into changing the first user's behavior, and/or characterize any other useful mental, emotional, or even physical attribute of the first user.

Figure 5:
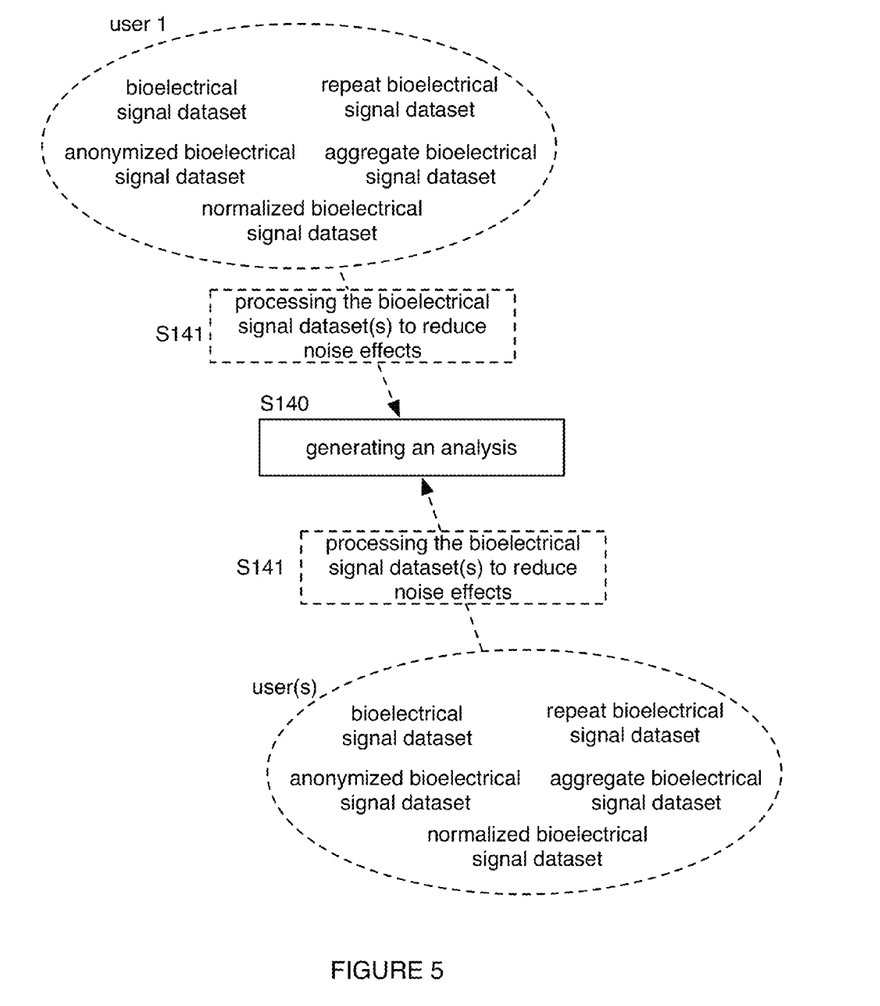
FIG. 5 is a flowchart representation of an embodiment of a portion of a method for instructing a behavior change in a user.

Step S140 recites generating an analysis based upon the bioelectrical signal dataset, and functions to generate a collaborative analysis of the first user's bioelectrical signal data. In Step S140, the analysis preferably takes supplementary data (e.g., of an augmented dataset) into account; however, the analysis can also be generated based upon a non-augmented bioelectrical signal dataset. As shown in FIG. 5, Step S140 can further comprise processing the bioelectrical signal dataset to reduce noise effects S141. In one variation, processing can comprise filtering, compressing, analyzing, or comparing multiple bioelectrical signal datasets, taken within multiple time windows, against baseline bioelectrical signal data to reduce noise. In another variation, processing can further comprise aggregating and/or averaging bioelectrical signal data from the first user and/or multiple users in order to minimize the effect of random or unwanted variation on measures or conclusions derived from the data.

In some variations, the analysis can be generated based upon comparisons between multiple datasets (e.g., from a single or multiple users) to extract information related to trends in signals correlated, for example, with different brain regions. In one example, brain activity, as characterized by EEG signal data, can be isolated for general regions of the brain, such as the forebrain, midbrain, and hindbrain, for particular regions of the brain, such as the frontal, temporal, parietal, or occipital lobe of the cerebral cortex, for more specific portions of the brain, such as the left or right parietal lobe, or for any other portion of the brain of any other focus. Brain activity can also be isolated indicating functional connectivity or interaction between multiple portions of the brain. Stimuli and actions, such as playing a piano, reading a book, watching a commercial or sporting event, eating, studying, drawing, cooking, talking with friends, etc., can then be associated with brain activity in a particular portion of the brain. A multidimensional matrix of stimulus, action, environmental condition, related user experience, etc. over time can be assembled to quantitatively and/or qualitatively relate certain brain activity to a particular user experience and to depict changes in user brain activity over time given the particular user experience. Additionally, comparing bioelectrical signal data taken at multiple time points and associated with similar actions can further allow trends in brain activity over time (e.g., over days, weeks, or years) to be extracted despite signal noise.

Furthermore, as shown in FIG. 1A, Step S140 can further comprise Step S145, which recites guiding the second user through the analysis of the data of the first user. The data of the first user preferably comprises an augmented dataset including bioelectrical signal data from the first user; however, the data of the first user can alternatively comprise any other suitable data and/or data of other users. In one example, trends in data of the first user can be presented (e.g., rendered at a user interface of the second user) in graphical form against trends in data for other users, such as of an age, education level, mental disorder, or other demographic similar to that of the first user. In the example, the second user can be visually guided through comparative analyses of the trends at the user interface, using signal processing tools and indicators (identifiers) that direct the second user's attention toward specific portions of the data (e.g. portions containing significant similarities or differences in data across users and/or actions, regions of interest). In the example, abnormalities (e.g., outliers) can also be isolated in an automated or manual manner, and similar cases in other users can be indicated to or retrieved for the second user. Additional user- or action-related information can be associated with particular portions of the data of the first user and patterns can be extracted for certain actions, stimuli, moods, cultural backgrounds, interests, marital statuses, medical histories, illnesses, locations, habits, diets, weather, etc. Any of these analytics, trends, patterns, or data can be presented to the second user in the example of Step S145, such as on a display of an electronic device (e.g., computer, tablet, or smartphone), in order to guide cooperative analysis of the data by the first and the second users.

Step S140 can thus comprise generating an analysis based upon data including bioelectrical signal data and other data (e.g., biosignal, biometric, and environment data), data associated with one action or multiple actions (e.g., to determine a convergence or divergence in signals associated with multiple actions), and data collected from a single user or multiple users (e.g., aggregate bioelectrical signal data). The analysis can further be generated according to any suitable combination of the embodiments, variations, and examples described above, using independent components analysis, or using any suitable method, such as those described in U.S. patent application Ser. No. 13/903,382, entitled "System and Method for Instructing a Behavior Change in a User" and U.S. Pat. Pub. No. 2013/0035579, entitled "Methods for Modeling Neurological Development and Diagnosing a Neurological Impairment of a Patient", which is incorporated herein in its entirety by this reference.

Step S150 recites transmitting the analysis to at least one of the first user and a third entity, and functions to further facilitate collaborative communications between the second user and another entity, in relation to the analysis generated in Step S140. In Step S150, the analysis is preferably transmitted to an electronic device of the first user and/or third entity. The electronic device of the first user is also preferably Internet-capable and presents the analysis to the first user through a web browser or application executing on the electronic device. Preferably, the analysis is transmitted and rendered visually at a display of the electronic device, by way of an application or other software module executing at the electronic device. In some variations, the transmitted analysis can comprise a graphic that qualitatively and/or quantitatively characterizes the analysis, for example, by way of a displayed graph, metric, picture, or text description of the analysis. The analysis, however, can alternatively be rendered or transmitted in any suitable manner, such as by way of an audio transmission.

Step S160 recites facilitating a communication, related to the analysis, between at least two of the second user, the first user, and the third entity, which functions to further enable cooperative analysis of the data of the first user. Through Steps S150 and S160, the first and second users and/or any other suitable entity can cooperatively: compare data of the first user collected within multiple time windows, compare data from the first user with data from other users, or analyze data associated with multiple actions; design or designate new actions for the first user to perform while an additional bioelectrical signal dataset is collected; verify effects of user behavior and/or changes in user behavior on brain function; verify effects of medications on user brain function; diagnose a disease or disorder and verify efficacy of treatment based upon brain activity; or perform any other relevant act or test any other variable, behavior, action, medication, or treatment. In light of these examples, Steps S150 and S160 can thus be repeatedly or iteratively performed, in a manner that generates multiple evolving analyses based upon repeat communications between the second user, the first user, and/or any other entity.

The communication in Step S160 is preferably enabled using electronic devices of the first user, the second user, and/or any additional entity; but can be enabled in any suitable manner. In variations of Step S160 using electronic devices, a module enabling the communication (e.g., web browser, application) preferably also support(s) video conferencing, audio conferencing, email, instant messaging, or other audio-, visual-, or text-based communication (e.g., with a messaging client) between the communicating entities. This communication can also be private, semi-private, or public and can be encrypted according to any of a variety of authentication and encryption schema. Furthermore, any communications or transmissions in Steps S130, S150 and S160 preferably occur in real time or near real time. For example, an EEG signal of the first user can be transmitted to the second user substantially in real time in Step S130 and substantially immediately reviewed by the second user in Step S130, wherein the first and second users can subsequently analyze the EEG signal together through a line of communication enabled by Steps S150 and Step 160. The communication, however, can occur in a non-real-time manner.

In variations of the method 100 comprising Step 112, which recites providing a stimulus, the method 100 can further comprise Step S170, which recites providing a modified stimulus to the first user based upon at least one of the analysis and the communication. Step S170 functions to generate a modified response by the first user, such that bioelectrical signal data associated with the modified stimulus can be further collected and analyzed. The stimulus in Step S170 is preferably provided in the same manner by which the stimulus is provided in Step S112; however, the stimulus in Step S170 is preferably characterized by a measurable adjustment, such that is associated with, but different from the stimulus provided in Step S112. The modified stimulus, can, however, be replaced with a repeat of the stimulus provided in Step S112, in variations wherein the original stimulus was shown to have a desired effect. In a first example, the stimulus in Step S112 is a music sample provided while the user is exercising, and the modified stimulus in Step S170 comprises music samples similar to the music sample of Step S112, in response to analyses and communications that showed that the first user responded positively to the initial stimulus. In a second example, the stimulus in Step S112 is a first stress reduction therapy, and the modified stimulus in Step S170 is a second stress reduction therapy, in response to analyses and communications that showed that the first user had little response to the first stress reduction therapy. The modified stimulus provided in Step S170 can, however, comprise any other suitable modified stimulus based upon analyses generated in Step S140 and/or communications resulting from Steps S150 and S160.

The method 100 can further comprise any other suitable step, including storing the bioelectrical signal dataset on a digital medical record of the first user, uploading the analysis to a profile of the first user on a social media website or service (e.g., a service associated with data of the first user on a data storage module), and/or transmitting, uploading, or storing the data by any other suitable system, network, server, service, or device. Additionally, any analysis methods, including the software, tools, program, or algorithm used by the second user or other entity to perform analysis of the data of the first user, can also be transmitted to the first user or to additional users, associated with data of the first user on a data storage module, uploaded to a profile of the second user or any other entity on a social media website or service, or transmitted to, uploaded onto, or stored on or by any other system, network, server, service, or device. Any analysis method can also be made available to an additional user, such as in exchange for a fee or for access to additional EEG data. The analysis can also be performed by the first or second user, performed by the third entity, or performed automatically by at the data storage module (e.g., remote server) or a related computer system, and results of this analysis can be provided to additional users, e.g. in exchange for a fee.

Furthermore, variations of the method 100 can additionally or alternatively omit, rearrange, or add steps in any suitable manner, and any subject (i.e., user or entity) of a step can be substituted for or supplemented with another subject in variations of the method 100. In one such alternative variation, the method 100 functions to support bioelectrical signal data analysis that is a personal experiment for the first user. In this alternative variation, the first user can generate, access, and analyze the data wholly independently of a second user. For example, the first user can track and maintain the effects of certain stimuli, behaviors, actions, and habits on mental, emotional, and physical health and development. In this alternative variation, data and other personal and action information can remain wholly private to the first user; however, the first user can also communicate with a second user or other entity to request help or guidance in analysis of data. Step S145 can also be tailored to the first user to aid the first user in independent analysis data and/or self-diagnosis of a particular condition or characteristic.

As a person skilled in the field of biosignals will recognize from the previous detailed description and from the figures and claims, modifications and changes can be made to the preferred embodiments of the method 100 without departing from the scope of this invention defined in the claims.

2. System

As shown in FIG. 6, an embodiment of a system 300 for providing and aggregating bioelectrical signal data comprises a biosignal detector 310 and a processor 320 comprising a receiver 330, an analyzer 340, a transmitter 350, and a stimulus transmission module 360. The system 300 can further comprise a data storage module 370 that receives data relevant to a user's behavior change. The system 300 functions to facilitate collection of bioelectrical signal data while a user engages in a particular action associated with the user's behavior change, to generate an analysis based upon bioelectrical signal and/or other data collected from the user, and to provide a behavior change suggestion to the user based upon the analysis. The system 300 preferably enables a variation of the method 100 described above, but can alternatively facilitate performance of any suitable method involving collection and analysis of bioelectrical signal data to promote a behavior change in a user.

The biosignal detector 310 functions to collect bioelectrical signal data from a user. The biosignal detector 310 preferably comprises a bioelectrical signal sensor system, wherein the sensor system comprises a plurality of sensors, each sensor providing at least one channel for bioelectrical signal capture. The plurality of sensors can be placed at specific locations on the user, in order to capture bioelectrical signal data from multiple regions of the user. Furthermore, the sensor locations can be adjustable, such that the biosignal detector 310 is tailorable to each user's unique anatomy. Alternatively, the sensor system can comprise a single bioelectrical signal sensor configured to capture signals from a single region of the user. In one example, the biosignal detector can be a personal EEG device, such as the Emotiv EPOC neuroheadset, which is shown in FIG. 2. EEG devices are taught in the U.S. Patent Publication Nos. 2007/0066914 (Emotiv) and 2007/0173733 (Emotiv), which are also incorporated in their entirety herein by this reference.

The biosignal detector 310 can also comprise or be coupled to additional sensor systems configured to capture data related to other biological processes of the user and/or the environment of the user. As such, the biosignal detector 310 can comprise optical sensors to receive visual information about the user's environment, GPS elements to receive location information relevant to the user, audio sensors to receive audio information about the user's environment, temperature sensors, sensors to detect MEG impedance or galvanic skin response (GSR), sensors to measure respiratory rate, and/or any other suitable sensor. Furthermore, the system can comprise multiple biosignal detectors, each paired with a given user, such that bioelectrical signal data can be simultaneously collected from more than one user.

The processor 320 comprises a receiver 330, an analyzer 340, a transmitter 350, and a stimulus transmission module 360, and functions to receive and process bioelectrical signal data, biosignal data, and/or any other suitable data from the user or group of users. As such, the processor 320 can comprise a remote server configured to perform the functions of at least one of the receiver 330, the analyzer 340, the transmitter 350, and the stimulus transmission module 360. In this embodiment, the remote server can execute analysis tools to facilitate processing, analysis, storage, and/or transmission of data; however, the processor 320 can alternatively comprise any other suitable element or combinations of elements.

The receiver 330 functions to receive bioelectrical signal datasets from a single user or multiple users. The receiver 330 preferably comprises a wireless connection to a biosignal detector (or other suitable element for data transfer); however, the receiver 330 can alternatively comprise a wired connection. In wireless variations, the receiver 330 can implement wireless communications, including Bluetooth, 3G, 4G, radio, or Wi-Fi communication. In these variations, data and/or signals are preferably encrypted before being received by the receiver 330. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

The analyzer 340 functions to generate an analysis of collected bioelectrical signal data and any other biosignal, biometric, and/or environment data from the user(s), in order to provide the basis for a behavior change suggestion. In some variations, the analyzer 340 can further function to generate the behavior change suggestion, an adherence metric, and/or an analysis based upon the adherence metric to a user. The analyzer 340 preferably implements signal analysis techniques (e.g., independent component analysis) and data mining algorithms; however, the analyzer 340 can additionally or alternatively implement any suitable methods or algorithms for processing and/or comparing bioelectrical signal datasets. In a first variation, the analyzer 340 is configured to generate an analysis based upon multiple bioelectrical signal datasets collected from a single user. In a second variation, the analyzer 340 is configured to generate an analysis based upon bioelectrical signal datasets from multiple users.

The transmitter 350 functions to transmit at least one of a generated analysis and a behavior change suggestion to the user. As such, the transmitter is preferably configured to communicate with a device of the user in order to electronically provide the analysis and/or behavior change suggestion at a user-device interface. In other variations, the transmitter can provide the analysis and/or behavior change suggestion to an intermediate entity (e.g., storage module, third party) that further conveys the analysis/behavior change suggestion to the user. The transmitter 350 can alternatively comprise any other suitable element(s) configured to transmit information to a user.

The stimulus transmission module 360 functions to facilitate provision of a stimulus or combination of stimuli to a user, in order to prompt an action by the user related to the user's behavior change. As such, the stimulus transmission module 360 can comprise an alert system that provides a notification to the user, a module that gives a command to the user instructing the user to perform an action, a haptics system configured to provide haptic stimulus, a display configured to render a visual stimulus, an audio system configured to provide an audio stimulus, and/or any other suitable stimulus transmission system. Preferably, the stimulus transmission module comprises a controller that controls delivery of the stimulus/stimuli, with regard to timing, frequency, and/or duration. In one variation, at least a portion of the stimulus transmission module 360 is implemented on a mobile device of the user, or a set of mobile devices of a group of users, such that a given stimulus or combination of stimuli can be deployed whenever a user or group of users is using the mobile device(s). The system 300 can, however, comprise any other suitable stimulus transmission elements to provide a stimulus to one or more users.

The system 3O0 can further comprise a data storage module 370, which functions to receive and store data associated with the user's behavior change. Preferably, bioelectrical signal data and other enriching data is transmitted to and maintained by the data storage module 370. Furthermore, the data storage module 370 is preferably remote from the biosignal detector 310. As such, bioelectrical signal data of the first user and multiple other users are preferably collected over time and stored by the data storage module 370 at a remote location. The data storage module also preferably maintains aggregate bioelectrical signal data including anonymized (e.g., stripped of personal or identifying information) data of the first user and other users, wherein the aggregate data is preferably assembled into buckets defining a particular action or group of similar actions performed by users during recordation of bioelectrical signals. In some variations, the data storage module 370 can be a remote server configured to host or communicate with an application programming interface (API), wherein the API allows accessing and manipulation of data stored in the data storage module 370. In one example, the biosignal detector 310 can be Internet-capable and transmit data directly to the data storage module 370, or the biosignal detector 310 can communicate via a wireless or wired connection with a local electronic device, such as a smartphone or tablet, that transmits the data to the data storage module 370. In the example, the data storage module can thus be hosted by a remote server in a manner compliant with privacy laws (e.g., HIPAA compliance) or can be hosted in any suitable cloud storage module. Alternatively, bioelectrical signal data and additional enriching data can be maintained by a data storage module 370 that operates, at least in part, on an electronic device that is local to the user and configured to communicate with the biosignal detector 310. In any of the foregoing variations, the bioelectrical signal data and enriching data is preferably accessible by the user, from the data storage module 370, to view, augment, or update any portion of the data. Data can be transmitted to the data storage module 370 substantially in real time, such as during recordation of the signal, or once the data collection is completed, verified, or released by the user.

The system 300 can also further comprise a communications module 380, which functions to enable a communication between the first user and a second user and/or other entity. The communications module 380 is preferably integrated with a user interface provided by an application or software module executing on mobile devices of entities participating in the communication; however, the communications module 380 can alternatively comprise any other suitable element. The communications module 380 can be a message client that hosts audio-, video-, and/or text-based communication and can communicate with a server of a message service provider, server of a mailbox service that is a proxy for the message service provider, or any suitable messaging service. Furthermore, the message client can enable sending and receiving of messages, and can incorporate messages into a rendered interface (e.g., of a mobile device application and/or web browser application).

The method 100 and system 300 of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor 320 and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals will recognize from the previous detailed description and from the figures and claims, modifications and changes can be made to the preferred embodiments of the invention without departing from the scope of this invention defined in the following claims.

I claim:

1. A method for enabling collaborative analysis of EEG biosignal data between a first user associated with a first user device, and a second user associated with a second user device, the method comprising:
   providing a user interface to the second user, wherein the user interface is accessible over the Internet by the second user device;
   establishing an electrical interface between an EEG biosignal neuroheadset and a body region of the first user proximal the head region of the first user;
   defining a physical activity;
   providing, at an audio system of the EEG biosignal neuroheadset, an audio stimulus to the user, wherein the audio stimulus is configured to prompt a physical activity by the first user;
   at the EEG biosignal neuroheadset, automatically collecting an EEG bioelectrical signal dataset from the first user as the first user performs the physical activity;
   at a motion sensor of the EEG biosignal neuroheadset, automatically collecting a motion dataset from the first user as the first user performs the physical activity;
   at a remote server distinct from the first user device and the second user device:
      identifying the physical activity based on the motion dataset;
      augmenting the EEG bioelectrical signal dataset with additional data and information associated with the identified physical activity to produce an augmented dataset, wherein the additional data comprises the motion dataset;
      transmitting, via a wireless communicable link with the second user device, the augmented EEG dataset to the second user device, wherein the augmented dataset is presented to the second user through the user interface accessible over the Internet by the second user device;

at the user interface, guiding the second user through a first EEG analysis of the augmented EEG dataset, wherein guiding the second user comprises graphically presenting an EEG biosignal trend in the augmented EEG dataset;

transmitting, at the remote server, the first EEG analysis to the first user device;

facilitating a wireless digital communication, related to the first EEG analysis, between the first user and the second user, wherein facilitating the wireless digital communication comprises presenting data from the first EEG analysis to the first user at the first user device during the wireless digital communication; and providing, at the audio system of the EEG biosignal neuroheadset, a modified audio stimulus to the first user based upon the wireless digital communication, wherein the modified stimulus is different from the stimulus.

2. The method of claim 1, wherein automatically collecting the bioelectrical dataset comprises providing an additional stimulus configured to prompt the physical activity by the first user.

3. The method of claim 2, further comprising detecting a user event based on an analysis of at least one of biometric data and environmental data, wherein providing the additional stimulus comprises providing at least one of a haptic stimulus, a visual stimulus, and a user device auditory stimulus at the first user device, upon detection of the user event, wherein the environmental data pertains to environmental conditions proximal the first user as the first user performs the physical activity.

4. The method of claim 2, wherein providing the additional stimulus comprises providing the additional stimulus at the first user device based on received GPS data.

5. The method of claim 2, wherein providing the audio stimulus comprises providing a music sample.

6. The method of claim 1, wherein augmenting the EEG bioelectrical signal dataset comprises augmenting the EEG bioelectrical signal dataset from the first user with at least one of biometric data and environment data simultaneously collected from the first user to produce the augmented EEG dataset.

7. The method of claim 1, wherein transmitting the augmented EEG dataset to the second user device comprises transmitting a portion of the augmented EEG dataset to the second user device upon receiving, at the first user device, a manual input by the first user permitting release of the portion by the first user.

8. The method of claim 1, wherein transmitting the augmented EEG dataset to the second user device comprises transmitting the augmented EEG dataset to a second user and a third entity.

9. The method of claim 1, wherein guiding the second user through the first analysis of the augmented EEG dataset comprises directing the second user toward selected data from the augmented EEG dataset by graphically presenting data from the augmented EEG dataset to the second user and indicating regions of interest to the second user at the user interface accessible over the Internet by the second user device.

10. The method of claim 1, wherein the first user device is a mobile device of the first user.

11. The method of claim 1, wherein collecting the EEG bioelectrical signal dataset, transmitting the first analysis, and facilitating the communication are performed substantially in real time.

12. The method of claim 1, wherein facilitating a communication comprises facilitating the communication by way of a message client executing on at least one of: the first user device and the second user device.

13. The method of Claim 12, further comprising generating a second analysis based upon the communication.

14. The method of claim 1, further comprising storing a method of generating the first analysis on a data storage module and providing the method of generating the first analysis to a receiving entity.

15. A method for enabling collaborative analysis of bioelectrical signal data, the method comprising:

establishing an electrical interface between an EEG biosignal neuroheadset and a body region of a first user proximal the head region of the first user;

providing, at an audio system of the EEG biosignal neuroheadset, an audio stimulus to the first user, wherein the audio stimulus is configured to prompt a physical activity by the first user;

at the EEG biosignal neuroheadset, automatically collecting an EEG bioelectrical signal dataset from the first user as the first user performs the physical activity;

at a motion sensor of the EEG biosignal neuroheadset, automatically collecting a motion dataset from the first user as the first user performs the physical activity;

identifying, at a remote server, the physical activity based on the motion dataset;

augmenting, at the remote server, the EEG bioelectrical signal dataset with additional data and information associated with the identified physical activity to produce an augmented EEG dataset, wherein the additional data comprises the motion dataset;

at a user interface of a user device associated with the first user and distinct from the remote server, guiding the first user through an analysis of the augmented EEG dataset, wherein guiding the first user comprises graphically presenting an EEG biosignal trend in the augmented EEG dataset;

at a processor coupled to the user interface, generating an association between the audio stimulus and the augmented EEG dataset, based upon the analysis;

facilitating a communication, related to at least one of the analysis and the association, between the first user and a second user; and providing, at the audio system of the EEG biosignal neuroheadset, a modified audio stimulus to the first user based upon at least one of the analysis, the association, and the communication, wherein the modified stimulus is different from the stimulus.

16. The method of claim 15, further comprising:

detecting a user event based on an analysis of at least one of biometric data and environmental data; and providing an additional stimulus, wherein the additional stimulus comprises at least one of a haptic stimulus, a visual stimulus, and a user device auditory stimulus at the user device of the first user, upon detection of the user event, wherein the environmental data pertains to environmental conditions proximal the first user as the first user performs the physical activity.

17. The method of claim 15, wherein automatically collecting the EEG bioelectrical signal dataset from the first user comprises:

upon detection of initiation of the physical activity performed by the first user, automatically initiating collection of the EEG bioelectrical signal dataset; and automatically terminating collection of the EEG bioelectrical signal dataset from the first user upon detection of termination of the physical activity performed by the first user.

18. The method of claim 15, wherein augmenting the EEG bioelectrical signal dataset comprises augmenting the EEG bioelectrical signal dataset from the first user with at least one of biometric data and environment data simultaneously collected from the first user to produce the augmented dataset.

19. The method of claim 15, wherein guiding the first user through an analysis of the augmented EEG dataset comprises directing the first user toward selected data from the augmented EEG dataset by graphically presenting data to the first user and indicating regions of interest to the second user at the user interface.

* * * * *